United States Patent
Bredno et al.

(10) Patent No.: US 9,299,171 B2
(45) Date of Patent: Mar. 29, 2016

(54) ADAPTIVE CALIBRATION FOR TOMOGRAPHIC IMAGING SYSTEMS

(75) Inventors: Joerg Bredno, San Francisco, CA (US); David Sowards-Emmerd, San Jose, CA (US); Jason Stephen Wiener, Fremont, CA (US); Eberhard Sebastian Hansis, Menlo Park, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 14/007,755

(22) PCT Filed: Apr. 2, 2012

(86) PCT No.: PCT/IB2012/051589
§ 371 (c)(1),
(2), (4) Date: Sep. 26, 2013

(87) PCT Pub. No.: WO2012/137121
PCT Pub. Date: Oct. 11, 2012

(65) Prior Publication Data
US 2014/0014828 A1 Jan. 16, 2014

Related U.S. Application Data

(60) Provisional application No. 61/471,905, filed on Apr. 5, 2011.

(51) Int. Cl.
*G01D 18/00* (2006.01)
*G06T 11/00* (2006.01)
(Continued)

(52) U.S. Cl.
CPC ............ *G06T 11/005* (2013.01); *A61B 6/032* (2013.01); *A61B 6/037* (2013.01); *A61B 6/4085* (2013.01); *A61B 6/4417* (2013.01); *A61B 6/5205* (2013.01); *A61B 6/582* (2013.01);
(Continued)

(58) Field of Classification Search
CPC ...... G06T 11/005; A61B 8/587; G06F 19/321
USPC ........................ 250/252.1, 362, 363.01–363.1
See application file for complete search history.

(56) References Cited

U.S. PATENT DOCUMENTS 4,875,165 A * 10/1989 Fencil et al. ................... 345/424
5,450,461 A * 9/1995 Hsieh ............................... 378/19
(Continued)

OTHER PUBLICATIONS

Buck, A. K., et al.; SPECT/CT; 2008; Journal of Nuclear Medicine; 49(8)1305-1319.
(Continued)

*Primary Examiner* — Kiho Kim

(57) ABSTRACT

A method comprises: acquiring imaging data using a tomographic radiological imaging apparatus (10); updating a calibration (42, 52) based on current information about the imaging apparatus; calibrating the imaging data using the up-to-date calibration; and reconstructing the calibrated imaging data to generate an image. The updating may be based on a current state of an idle or parked imaging modality that is not used in acquiring the imaging data, or on a measurement acquired together with the imaging data, or on the imaging data itself. For cone-beam computed tomography (CBCT) imaging data, the updating may comprise determining an intensity scale based upon intensity of at least one air pixel measured during the acquiring of the CBCT imaging data and updating an air scan template (60) by the intensity scale.

18 Claims, 4 Drawing Sheets

Figure 1:
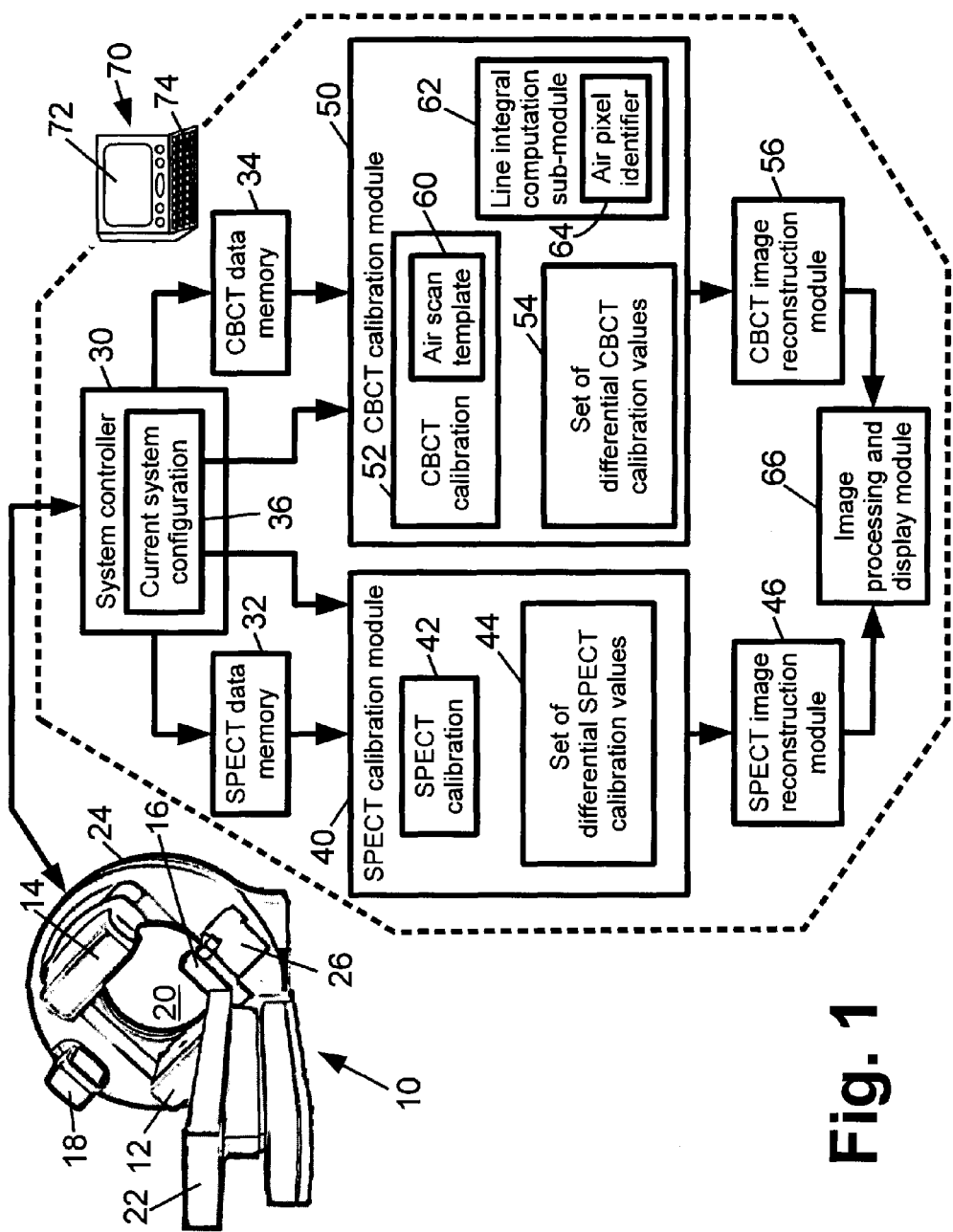

(51) Int. Cl.
*A61B 6/03* (2006.01)
*A61B 6/00* (2006.01)
*A61B 6/06* (2006.01)
*A61B 5/00* (2006.01)

(52) U.S. Cl.
CPC ............... *A61B 5/0035* (2013.01); *A61B 6/06* (2013.01); *A61B 6/4291* (2013.01)

(56) References Cited

U.S. PATENT DOCUMENTS

| | | |
|---|---|---|
| 5,481,115 A | 1/1996 | Hsieh et al. |
| 6,140,650 A | 10/2000 | Berlad |
| 7,086,780 B2 | 8/2006 | Wu et al. |
| 7,177,390 B2 | 2/2007 | Martin et al. |
| 7,494,276 B2 | 2/2009 | Borgmann et al. |
| 7,697,658 B2 | 4/2010 | Wang et al. |
| 7,840,051 B2 * | 11/2010 | Razeto ............ 382/131 |
| 2005/0226369 A1 | 10/2005 | Martin et al. |
| 2005/0259784 A1 | 11/2005 | Wu et al. |

OTHER PUBLICATIONS

Dong, H.; The Hounsfield Unit (HU) accuracy in Varian's cone-beam CT (CBCT) and its effect on dosimetric verification; 2006; Medical Physics; 33(6)2049.

Hsieh, J.; Computed Tomography: Principles, Design, Artifacts, and Recent Advances; 2009; Wiley Interscience; Chapter 2.3 Measurement of line integrals and data computing; pp. 42-46.

Zhang, L., et al.; Cone Beam CT Hounsfield Unit to Electron Density Calibration and Its Impact on Dose Calculation Accuracy; 2010; American Association of Physics in Medicine; abstract.

* cited by examiner

ADAPTIVE CALIBRATION FOR TOMOGRAPHIC IMAGING SYSTEMS

CROSS REFERENCE TO RELATED APPLICATIONS

This application is a national filing of PCT application Serial No. PCT/IB2012/051589, filed Apr. 2, 2012, published as WO 2012/137121 A1 on Oct. 11, 2012, which claims the benefit of U.S. provisional application Ser. No. 61/471,905 filed Apr. 5, 2011, which is incorporated herein by reference.

The following relates to the tomographic radiological imaging arts, transmission computed tomography arts, and related arts.

In tomographic imaging employing one or more moving detectors, the detector or detectors acquire imaging data while moving around an imaging subject so as to acquire views from different vantage points (sometimes called "frames"). Alternatively, the tomographic imaging can be performed using a ring of stationary detectors, as is conventional in positron emission tomography (PET) imaging. In the case of tomographic radiological imaging by magnetic resonance (MR), the detectors are radio frequency receive coils, which are usually (although not necessarily) stationary. The tomographic imaging data are reconstructed using suitable image reconstruction techniques to generate a three-dimensional image of the subject.

In emission tomographic imaging techniques, a radioemissive substance is administered to the subject and the one or more detectors detect radioemissions emanating from the subject. PET is an example of radioemission tomographic imaging. Another example of such a technique is single photon emission computed tomography (SPECT), which typically employs one or more moving gamma detector heads. These techniques generate an image of the distribution of the radioemissive substance in the subject, possibly modified by absorption or scattering in the subject. Some reconstruction techniques for emission imaging correct for absorption in the subject based on an absorption map of the subject.

In transmission tomographic imaging techniques, an external radiation source transmits radiation through the subject. A radiation detector is positioned opposite from the radiation source across the subject to detect the radiation after transmission through the subject. The radiation source and radiation detector move together around the subject while maintaining their relatively opposed orientation. An example of such a technique is transmission computed tomography with a flat panel detector or other two-dimensional detector array, also referred to as cone-beam CT (CBCT). These techniques generate an "absorption" image in which voxel values indicate local strength of absorption for the transmitted radiation, which is usually x-ray radiation.

Accurate tomographic radiological imaging relies upon accurate calibration of numerous aspects of the imaging system, such as geometrical parameters (e.g., detector position as a function of viewing frame), detector gain, shading effects of auxiliary components such as anti-scatter grids or collimators, and so forth. In the case of transmission imaging modalities, additional parameters relate to the radiation source, such as x-ray tube focal spot position and x-ray output intensity.

Typically, a calibration for such parameters is performed on-site by the end-user (e.g., hospital radiology staff) or by a field engineer employed by the imaging system manufacturer. The calibration is typically performed when the imaging system is installed, and is repeated during imaging system modification or maintenance events. The calibration values are stored in a suitable memory and are recalled and applied to acquired tomographic radiological data prior to or during image reconstruction.

The following provides new and improved apparatuses and methods as disclosed herein.

In accordance with one disclosed aspect, a method comprises: acquiring imaging data using a tomographic radiological imaging apparatus; updating a calibration based on current information about the tomographic radiological imaging apparatus to generate an up-to-date calibration; calibrating the imaging data using the up-to-date calibration to generate calibrated imaging data; and reconstructing the calibrated imaging data to generate an image. The updating may be based on a current state of an idle or parked imaging modality that is not used in acquiring the imaging data, or on a measurement acquired together with the imaging data, or on the imaging data itself. In the case of CBCT imaging data, the calibration may comprise an air scan template, and the updating may comprise determining an intensity scale based upon intensity of at least one air pixel measured during the acquiring of the CBCT imaging data and updating the air scan template by the intensity scale.

In accordance with another disclosed aspect, a system comprises a tomographic radiological imaging apparatus and a processing device configured to cooperate with the tomographic radiological imaging apparatus to perform a method as set forth in the immediately preceding paragraph. In accordance with another disclosed aspect, a storage medium stores instructions executable by a digital processing device to perform a method as set forth in the immediately preceding paragraph.

In accordance with another disclosed aspect, a system comprises: a tomographic radiological imaging apparatus configured to acquire imaging data; a calibration module configured to update a calibration based on at least one of (i) a configuration of an idle or parked imaging modality of the tomographic radiological imaging apparatus that is idle or parked at the time of acquisition of the imaging data, (ii) a measurement acquired together with the imaging data, and (iii) the imaging data, and calibrate the imaging data using the updated calibration; and an image reconstruction module configured to reconstruct the calibrated imaging data to generate an image. In some such embodiments, the tomographic radiological imaging apparatus is configured to acquire cone-beam computed tomography (CBCT) imaging data, the calibration comprises at least an air scan template, and the calibration module is configured to update the air scan template by applying an intensity scaling, which may be computed based on one or more air pixels extracted from a frame of the CBCT imaging data.

One advantage resides in more accurate tomographic radiological imaging data and consequently more accurate images.

Another advantage resides in better stability of tomographic radiological imaging over the course of an imaging session or sequence of imaging sessions.

Further advantages will be apparent to those of ordinary skill in the art upon reading and understanding the following detailed description.

FIG. 1 diagrammatically shows a SPECT/CBCT imaging system including SPECT and CBCT calibration modules as disclosed herein.

Figure 2:
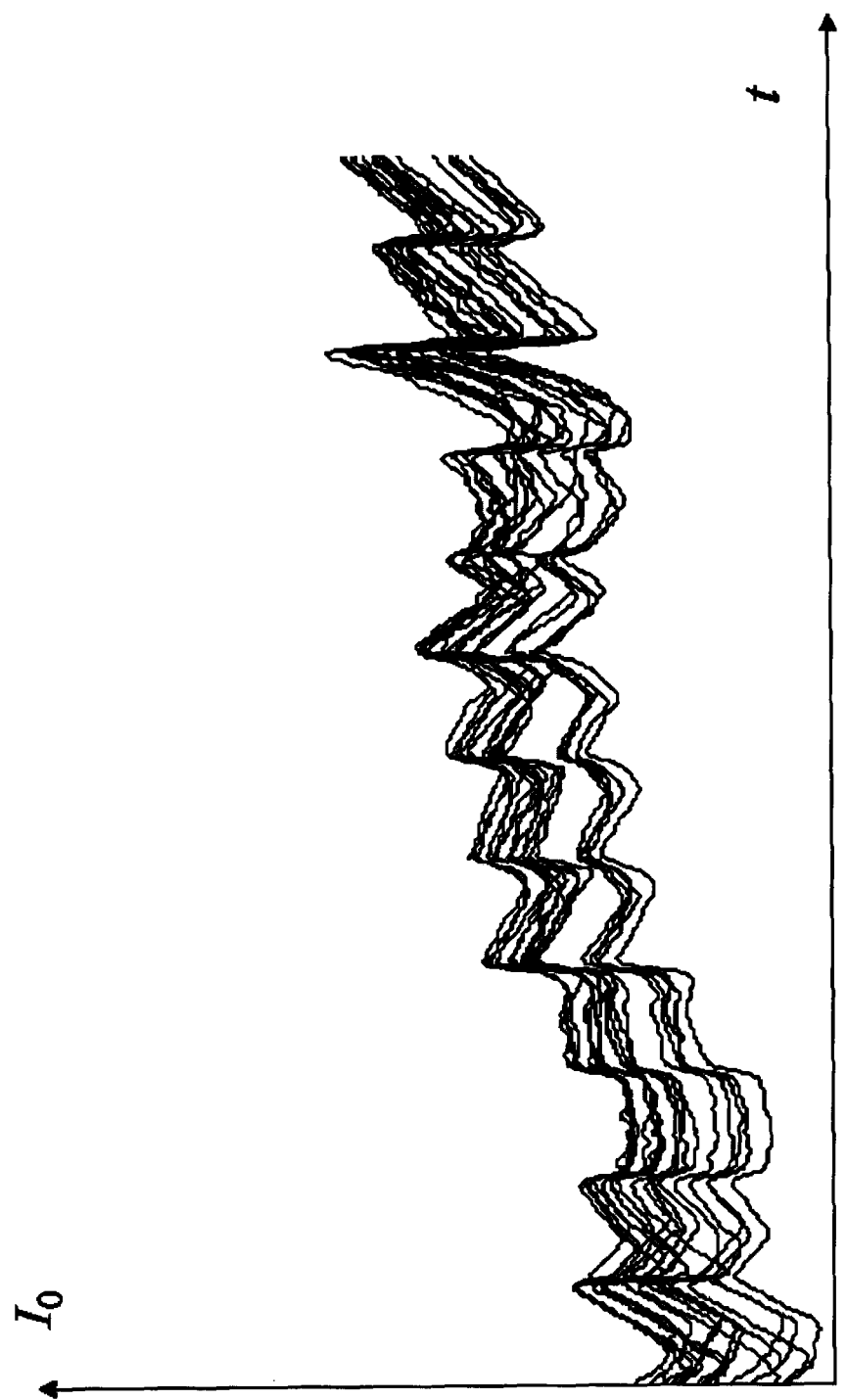

FIG. 2 shows several air scans each plotting no-load intensity $I_o$ measured as a function of scan time (or, equivalently, frame) for a selected detector pixel, with the several air scans acquired with different detector exposure histories.

Figure 3:
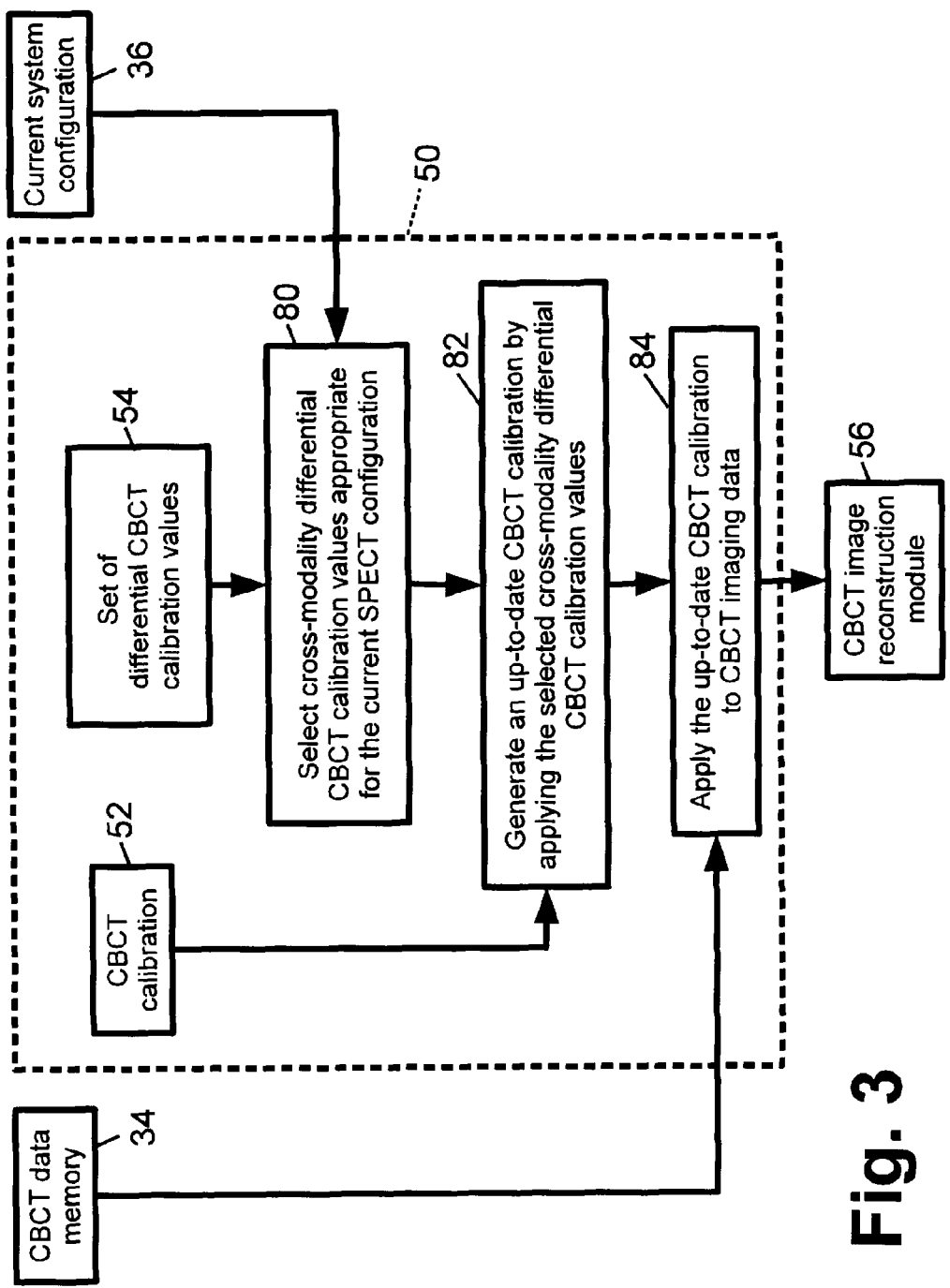

FIG. 3 diagrammatically shows operation of the cross-modality calibration aspect of the CBCT calibration module of the SPECT/CBCT system of FIG. 1.

Figure 4:
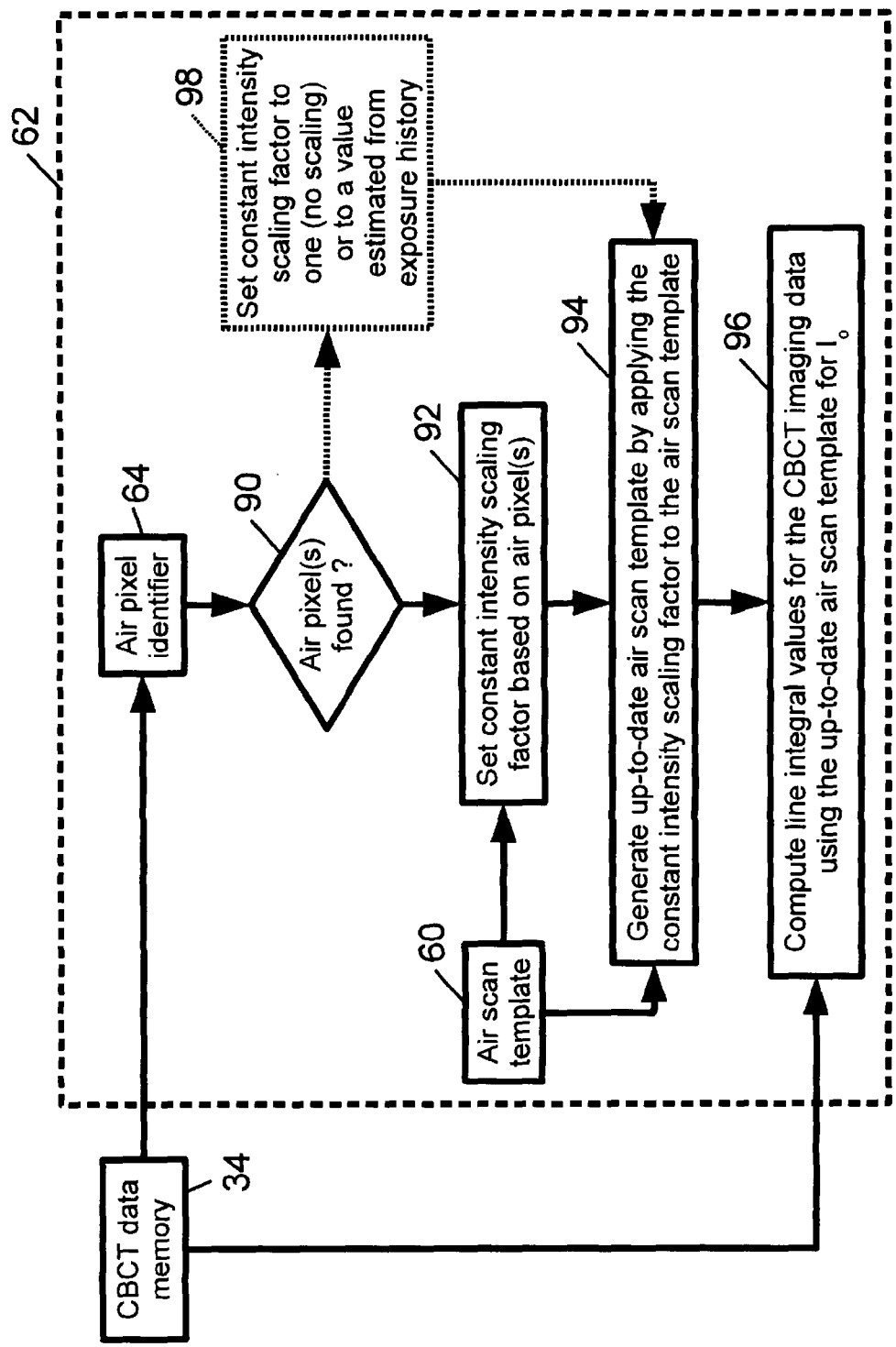

FIG. 4 diagrammatically shows operation of the line integral sub-module of the CBCT calibration module of the SPECT/CBCT system of FIG. 1.

The disclosed calibration approaches are generally applicable to substantially any single modality or multimodality tomographic radiogical imaging apparatus. By way of example, FIG. 1 illustrates a multimodality SPECT/CBCT imaging apparatus 10 that includes (1) a SPECT imaging modality comprising at least one SPECT detector head (namely two gamma detector heads 12, 14 in the illustrative apparatus 10) and (2) an CBCT imaging modality comprising a two-dimensional detector array 16 and corresponding radiation source 18 (e.g., an x-ray tube) mounted across an imaging space 20 from the CBCT detector array 16. The SPECT detector heads 12, 14 and the CBCT x-ray/detector 16, 18 are both arranged to image a subject disposed on a common table or subject support 22. The SPECT imaging modality 12, 14 and CBCT imaging modality 16, 18 are both mounted on a mechanical support structure 24 that includes suitable mechanical joints, rotating gantries, or so forth to enable the gamma detector heads 12, 14 to conformally orbit an imaging subject disposed on the table 22 and to enable the opposing radiation source 18 and detector array 16 to rotate in concert around the subject on the table 22. The illustrative SPECT/CBCT imaging apparatus 10 is a Brightview™ XCT SPECT/CT imaging system (available from Koninklijke Philips Electronics N.V., Eindhoven, The Netherlands).

The mechanical support structure 24 of the illustrative Brightview™ XCT SPECT/CT imaging system provides the SPECT detector heads 12, 14 with numerous degrees of motional freedom, for example enabling scans in which the SPECT detector heads 12, 14 are relatively oriented at either a 90° angle or a 180° angle, enabling the SPECT detector heads 12, 14 to independently move toward or away from the subject to provide conformal orbiting, enabling imaging of the subject with the table 22 in various positions, and so forth. In another SPECT operational mode, only a single SPECT detector head is used to perform a planar scan, for example in a whole-body bone imaging scan. During SPECT imaging the detector array 16 of the CBCT imaging modality can be rotated and parked in a recess 26 of the mechanical support structure 24 so that it does not interfere with the motion of the SPECT detector heads 12, 14. The SPECT modality is also designed to have various collimators (not shown) optimized for various imaging scan types mounted on the radiation-receiving faces of the detector heads 12, 14. The mechanical support structure 24 of the illustrative Brightview™ SPECT/CT imaging system also provides the CBCT imaging modality 16, 18 with substantial flexibility. For example, various anti-scatter grids (not shown) can be mounted on the radiation-receiving face of the detector array 16 to suppress X-ray radiation scattered in the scanned subject. The illustrative detector array 16 of the Brightview™ XCT imaging modality is a flat panel detector, and is arranged in an off-center geometry. The radiation source 18 (an x-ray tube in the illustrative Brightview™ XCT SPECT/CT imaging system) can be operated at various brightness levels to optimize signal while limiting radiation absorption by the subject.

In addition to having a wide range of user-selectable configurations, the illustrative multimodality tomographic radiological imaging apparatus 10 may exhibit operational drift as a function of usage history. For example, the brightness and/or focal spot position of the beam generated by the radiation source 18 can change depending upon tube load, temperature, and usage history. The CBCT detector array 16 can undergo various types of drift depending upon its recent exposure history, such as bright burn caused by filling of traps in the scintillator (the illustrative Brightview™ XCT SPECT/CT imaging system employs a CsI needle scintillator). Conventionally, the tomographic radiological imaging apparatus 10 is calibrated on-site by the end-user (e.g., hospital radiology staff) or by a field engineer employed by the imaging system manufacturer. Such calibration is typically performed when the imaging apparatus 10 is installed, and is repeated during various modification or maintenance events.

It is recognized herein, however, that such a calibration approach has substantial deficiencies. The calibration may fail to account for the impact of current imaging system conditions, or past imaging system history, on the current imaging data acquisition. For example, the CBCT detector array 16 can show "memory" effects due to a recent history of high x-ray exposure. Such memory effects may not be accommodated by a calibration acquired using the detector array 16 after a different recent exposure history.

Additionally, it is recognized herein that imaging data acquired by one modality (e.g., CBCT) may be affected by the current state of the other modality (e.g., SPECT). For example, the type of collimator mounted on the SPECT detector heads 12, 14 may impact the position of the CBCT detector array 16 and/or the radiation source 18 during CBCT imaging. Similarly, the "parked" position of the SPECT detector heads 12, 14 during CBCT imaging may affect the CBCT imaging data. Such "cross-modality" effects may not be corrected if the imaging data are acquired with the currently inoperative imaging system in a different state from the state used in acquiring the calibration. By way of illustrative example, a CBCT calibration acquired with the SPECT modality parked in one configuration may not accurately correct CBCT imaging data acquired with the SPECT modality parked in a different configuration.

Accordingly, the calibration approaches disclosed herein update the calibration for an active imaging modality based on current information about the inactive imaging or "parked" modality at the time of imaging data acquisition by the active imaging modality. The imaging data acquired by the active imaging modality are calibrated using the up-to-date calibration, and the calibrated imaging data are reconstructed to generate an image. In some embodiments the update of the calibration includes selecting a configuration-specific differential calibration corresponding to the configuration of the inactive or parked imaging modality at the time of the acquiring, and updating calibration parameters of the active modality calibration by differential calibration values of the differential calibration to generate the up-to-date calibration. In some embodiments, the calibration parameters are updated based on at least one of (i) a configuration of the inactive or parked tomographic radiological imaging apparatus at the time of acquisition of the imaging data, (ii) a measurement acquired together with the imaging data, and (iii) the imaging data. For example, in the case of CBCT imaging, in some embodiments the calibration update includes updating a calibration parameter of the CBCT calibration by a differential calibration value based upon an x-ray tube temperature provided by a temperature sensor measurement acquired together with the CBCT imaging data. In some embodiments, the calibration update includes updating a calibration parameter of the CBCT calibration by a differential calibration value based upon a configuration aspect of the inactive or parked SPECT modality 12, 14, such as the type of mounted collimator, or positioning of the SPECT detector heads 12, 14. In some embodiments, the imaging data are acquired by CBCT and the calibration update includes updating an air scan template based upon the intensity of at least one air pixel measured during the acquiring of the CBCT imaging data, or computed based upon exposure history of the radiation detector 16. The up-to-date air scan template determines the zero attenuation intensity ($I_o$) for computing the absorption line integral.

With continuing reference to FIG. 1, a system controller 30 controls the tomographic radiological imaging apparatus 10 to acquire imaging data. SPECT imaging data acquired by the SPECT imaging modality 12, 14 are suitably stored in a SPECT data memory 32, while CBCT imaging data acquired by the CBCT imaging modality 16, 18 are suitably stored in an CBCT data memory 34. Note that although the data memories 32, 34 are shown as separate elements in FIG. 1, in some embodiments a common physical memory may be organized into files, directories, folders, storage spaces, or otherwise logically partitioned to define the data memories 32, 34. The system controller 30 also stores a current system configuration 36 including configuration parameters such as accessories mounted on the radiation detectors (e.g., type of collimators, or lack thereof, mounted on the SPECT detector heads 12, 14, or type of anti-scatter grid, or lack thereof, mounted on the CBCT detector array 16), relative positioning of the SPECT detector heads 12, 14 (e.g., offset by 90°, offset by 180°, or so forth), an indication of whether the CBCT detector array 16 is parked in the storage recess 26, the current imaging scan selection, and so forth.

In the case of SPECT data, a SPECT calibration module 40 updates a SPECT calibration 42 based on a set of differential SPECT calibration values 44. Some of these differential SPECT calibration values 44 may be intra-modality differential SPECT calibration values that update the SPECT calibration 42 for differences between the current SPECT configuration and the SPECT configuration at the time the SPECT calibration 42 was generated. Additionally, some of these differential SPECT calibration values 44 are cross-modality differential SPECT calibration values that account for the impact on the SPECT imaging data of differences between the current CBCT configuration and the CBCT configuration at the time the SPECT calibration 42 was generated. The resulting up-to-date SPECT calibration is then applied to the SPECT data by the SPECT calibration module 40 to generate calibrated SPECT imaging data. A SPECT reconstruction module 46 reconstructs the calibrated SPECT imaging data to generate a SPECT image.

In the case of CBCT data, a CBCT calibration module 50 updates a CBCT calibration 52 based on a set of differential CBCT calibration values 54. Some of these differential CBCT calibration values 54 may be intra-modality differential CBCT calibration values that update the CBCT calibration 52 for differences between the current CBCT configuration and the CBCT configuration at the time the CBCT calibration 52 was generated. Additionally, some of these differential CBCT calibration values 54 are cross-modality differential CBCT calibration values that account for the impact on the CBCT imaging data of differences between the current SPECT configuration and the SPECT configuration at the time the CBCT calibration 52 was generated. The resulting up-to-date CBCT calibration is then applied to the CBCT data by the CBCT calibration module 50 to generate calibrated CBCT imaging data that is reconstructed by an CBCT reconstruction module 56 to generate an XCT image.

The disclosed provision for cross-modality differential calibration values is based on the insight that the imaging data acquired by an active modality may be impacted by the current configuration of the inactive (or parked) modality. If the inactive modality can be parked or left idle in various configurations (as is the case, for example, when parking the SPECT detector heads 12, 14 of the Brightview™ XCT SPECT/CT imaging system during CBCT imaging), then it is possible that the current configuration of the inactive modality may be different from the configuration of the inactive modality when the active modality calibration was generated. The cross-modality differential calibration values enable this differential impact on the active modality to be corrected.

In the case of CBCT, the calibration module 50 also performs an additional calibration as follows. The as-acquired CBCT imaging data are intensity measurements I, which are converted into absorption measurements prior to the reconstruction operation. The conversion is performed based on the Beer-Lambert law: $I = I_o \exp(-\int \mu dx)$, where $\mu$ is the linear attenuation coefficient, dx is signifies integration along an X-ray path, I is the intensity measured in the CBCT imaging data acquisition, and $I_o$ is the intensity that would have been measured if there was no absorbing material in the path of the transmitted x-ray. Assuming that $I_o$ is known, the Beer-Lambert law can readily be solved to yield $\int \mu \, dx = \log(I_o) - \log(I)$. This quantity is also known as the 'line integral' of the X-ray attenuation.

In order to compute the line integral, the value for $I_o$ must be known. Toward this end, the CBCT calibration 52 includes an air scan template 60 that is generated by performing an CBCT imaging data acquisition with no sample loaded (and with the table 22 withdrawn, if it is absorbing for x-rays). In this case all measured $I=I_o$. The air scan template 60 is measured for all frames (that is, all vantage points) and for each detector pixel of the CBCT detector array 16, since $I_o$ can vary for different detector pixels and for different frames.

With continuing reference to FIG. 1, it is recognized herein that the values of the air scan template 60 may be in error due to various sources of drift of $I_o$. For example, the value of $I_o$ may be affected by variation in the brightness of the beam generated by the radiation source 18 (which may, in turn be affected by tube heat load or tube temperature and/or by intentional adjustment of the beam current). The value of $I_o$ may also be affected by bright burn caused by filling of traps in the scintillator. The amount of bright burn is affected by the recent exposure history of the detector array 16.

With brief reference to FIG. 2, it is recognized herein that drift in $I_o$ can typically be represented by a scaling factor (at least to first order) that is constant across the detector (that is, for all detector pixels) and across frames. For example, FIG. 2 shows several air scans each plotting no-load intensity $I_o$ measured as a function of scan time (or, equivalently, frame) for a selected detector pixel, with the several air scans acquired with different detector exposure histories. It is seen that $I_o$ varies with detector exposure, but varies in the same way for all frames. As a result, drift in $I_o$ can be compensated by an approximately constant intensity scale in $I_o$ that is independent of detector pixel and frame.

With returning reference to FIG. 1, in view of the foregoing observations just set forth with reference to FIG. 2, the CBCT calibration module 50 further includes a line integral computation module 62 that computes the line integrals for the CBCT imaging data. In computing the line integrals, the line integral computation module 62 updates the air scan template 60 by applying a constant intensity scale to image values or a constant offset to line integrals. Since a constant additive offset in line integrals translates to an approximately constant additive offset in the reconstructed image, a suitably scaled offset can alternatively be applied after reconstruction of the XCT volume image. In one suitable embodiment, an air pixel identifier 64 searches the acquired CBCT imaging data to identify one or more "air pixels", that is, detector pixel measurements for which it is determined that there was no absorption and hence have $I=I_o$. Once an air pixel is identified by the air pixel identifier 64, its value is compared with the corresponding pixel of the corresponding frame of the air scan template 60—the ratio between these values is the constant intensity scale. The thusly updated air scan template is then used by the line integral computation module 62 to provide the $I_o$ values in computing the line integral values from the CBCT intensity measurements I. It is alternatively possible to apply the scaling factor as a constant offset to a reconstructed volume computed from the identified ratio between observed air pixels and $I_o$ from calibration With continuing reference to FIG. 1, an image processing and display module 66 suitably processes and/or displays the SPECT image, the CBCT image, or a fusion or other combination of SPECT and CBCT images. The various processing components 30, 40, 46, 50, 56, 66 are suitably embodied by a digital processing device 70 (optionally augmented with analog or hybrid digital/analog circuitry embodied by application-specific integrated circuitry, or ASIC, or other analog or hybrid components). The illustrative digital processing device is as an illustrative computer 70, which includes or has access to a hard disk drive, random access memory (RAM), FLASH memory, optical memory, or other data storage device or component (or combination thereof) suitably embodying the memory components 32, 34 and suitably storing the current system configuration 36 and calibrations 42, 44, 52, 54, 60. The computer or other digital processing device 70 also may include or have access to a display device 72 via which the image processing and display module 66 displays reconstructed images. The computer or other digital processing device 70 also may include or have access to a keyboard or other user input device or devices 74 via which a radiologist or other human user may interact with the system to operate the tomographic radiological imaging apparatus 10 to acquire imaging data and to calibrate and reconstruct imaging data and display reconstructed images. It will also be appreciated that the disclosed calibration techniques may be embodied by a storage medium (e.g., a magnetic medium such as a hard drive, or an electronic storage medium such as RAM or FLASH memory, or an optical memory, or so forth) storing instructions executable by a digital processing device 70 to perform various methods as disclosed herein.

With reference to FIG. 3, an illustrative example of the cross-modality calibration update aspect of the CBCT calibration module 50 is described. The calibration module 50 performs an operation 80 in which configuration-specific cross-modality differential CBCT calibration parameters are selected from the set of configuration-specific differential CBCT calibrations 54 based on the current configuration of the SPECT modality according to the current system configuration 36. In other words, the operation 80 selects cross-modality differential CBCT parameters that compensate for the effect of aspects of the current state of the idle or parked SPECT system on the active CBCT imaging. These aspects may include the type of collimator mounted on the SPECT detector heads 12, 14, the position calibration of the SPECT detector heads 12, 14, or so forth.

In an operation 82, the up-to-date CBCT calibration is generated by, for each CBCT calibration parameter, performing a differential update such as multiplying the calibration parameter value obtained from the (base) CBCT calibration 52 by a configuration-specific differential factor or factors provided by the selected configuration-specific differential CBCT calibration, or adding an offset or offsets provided by the differential calibration, or so forth. When two or more different differential corrections are to be applied to a single configuration parameter (for example, one differential correction due to the operational temperature and another differential correction due to the type of SPECT collimator currently mounted), they may be applied in various ways, such as by first adding the differential corrections and then multiplying by the sum. Alternatively, the calibration parameter can be multiplied by each differential correction in succession. In practice, the differential correction or corrections is (are) usually small, and so both approaches will produce similar results. Differential factors that are applied as additive offsets can be applied together.

An operation 84 then applies the up-to-date CBCT calibration generated by the operation 82 to the CBCT imaging data to generate calibrated CBCT imaging data that are then reconstructed by the CBCT image reconstruction module 56. The application of each calibration parameter depends upon the type of calibration being performed. For example, a detector position calibration parameter may be a position offset that is applied additively, whereas an intensity calibration may be applied multiplicatively.

While FIG. 3 illustrates the CBCT calibration module 50, operation of the SPECT calibration module 40 is analogous. Again, the selection of the configuration-specific differential calibration may take into account cross-modality configuration aspects, which in this case reflect the impact of the configuration of the CBCT imaging modality 16, 18 on the SPECT imaging data. For example, whether the detector 16 is parked in the recess 26 or remains in its extended position may impact the precise position of the SPECT detector heads 12, 14.

In constructing the set of configuration-specific differential calibrations 44, 54, the system state changes that cause changes to the calibration 42, 52 are identified. By way of illustrative example, some possibly relevant system state changes include: changes of overall system geometry when changing SPECT collimators on a SPECT/CBCT system; changes of overall system geometry when changing relative position of SPECT detectors (e.g. Rel-90 vs Rel-180) on a SPECT/CBCT system; changes to focal spot position of an x-ray tube depending on tube load and temperature; changes of overall system geometry when changing the anti-scatter grid on a C-arm X-ray imager; changes to overall system geometry caused by a heavy patient; or so forth. Changes to the system geometry or the position of the x-ray focal spot are expected to most strongly affect the geometric calibration and the rotational gain correction representing varying anti-scatter grid and beam shaper shading.

Once the system state changes relevant to calibration are identified, the sets of configuration-specific differential calibrations 44, 54 are generated. In one suitable approach, once before or during installation of the imaging apparatus 10 the affected calibration parameters of the calibrations 42, 52 are measured under the various changing imaging apparatus states. From this data, the relative or absolute change of calibration information due to imaging apparatus status changes is determined and used to construct the sets of configuration-specific differential calibrations 44, 54. For cross-modality differential calibration, e.g. calibrating the impact of different SPECT modality configurations on CBCT data, the CBCT calibration parameters are measured with the SPECT detector heads 12, 14 in different positions and with different mounted collimators and so forth in order to quantitatively measure effects of these various SPECT modality configurations on the CBCT calibration parameters.

If the base calibrations 42, 52 are to be recalibrated, these re-calibrations are performed in one fixed, pre-determined system configuration (e.g., with low tube temperature, a defined SPECT collimator on a CBCT system, and with no weight on the patient table). For imaging session, the current state of the imaging apparatus 10 is taken into account and the most recent calibration 42, 52 is updated in accordance with the selected configuration-specific differential calibration prior to calibrating the imaging data.

With reference to FIG. 4, an illustrative example of the line integral computation sub-module 62 is described. The line integrals are derived using $I_o$ values provided by the air scan template 60. More generally, a distinct air scan template 60 is acquired for each distinct CBCT acquisition type. Different air scan templates may be needed for different arrangements of pixel binning, when using different types of collimator, or when using different energy setting(s) (for example, different kVp, different filtration, or wedge), or so forth. Each air scan template is generated by an air scan comprising an acquisition at a fixed exposure with no attenuating material in the field of view. This provides the effective intensity seen by the detector as a function of gantry angle (or frame) and mA (or mAs) for each technique.

However, the air scan template 60 (or even different air scan templates for different CBCT acquisition types) does not account for drift in $I_o$ caused by bright burn or recent exposure history of the detector array 16. By way of illustrative example, FIG. 2 shows multiple air scan templates taken with the same exposure, but different detector exposure history. To correct for such effects, the line integral computation sub-module 62 invokes the air pixel identifier 64 to identify one or more air pixels in the acquired CBCT imaging data. The air pixel identifier 64 can detect air pixels by various methods, such as: (1) thresholding based on a minimum expected intensity value; (2) identifying pixels forming a flat local gradient (perhaps in combination with the thresholding); (3) identifying projections that are not expected to undergo any absorption based on a priori information such as the shape or maximum size of the imaging subject; (4) perseverance of values over multiple frames; or so forth. At a decision 90, it is determined whether any air pixels were identified. If so, then in an operation 92 the air pixel or air pixels is (are) used to set the constant intensity scaling factor for updating the air scan template. For a given air pixel, the corresponding pixel in the corresponding frame of the air scan template 60 is identified and the ratio between the air value and the template value is the constant intensity scale. If the air pixel identifier identifies more than one air pixel, this process can be repeated for each air pixel and the resulting plurality of constant intensity scale values averaged or otherwise aggregated. Once the intensity scale is set by the operation 92, the air scan template is updated in an operation 94 by applying the intensity scale to all values of the air scan template. The resulting up-to-date air scan template is applied in computing line integral values for the CBCT data in an operation 96.

If the decision 90 indicates that a suitable air pixel was not found in the acquired CBCT imaging data, an alternative path indicated in FIG. 4 by dotted lines may be followed. In an operation 98 that is alternative to the operation 92, the intensity scale is set based on a criterion other than an identified air pixel. For example, the intensity scale can be set based on a recently acquired scan, or can be estimated from an exposure history record, or so forth. Alternatively, the operation 98 can set the intensity scale to one (in which case effectively no correction for bright burn or other $I_o$ drift is performed). In either case, processing suitably flows to the operation 94 to apply the identity or other alternative constant intensity scale.

The disclosed calibration techniques have been described with reference to the illustrative SPECT/CT imaging apparatus 10 of FIG. 1. More generally, it is to be appreciated that the disclosed calibration techniques can be applied to any single modality or multimodality tomographic radiological imaging apparatus, such as a single modality SPECT apparatus, a single-modality PET apparatus, a single modality computed tomography (CT) apparatus (e.g., CBCT, fan-beam CT, or so forth), a single-modality MR imaging apparatus, or a dual modality or multi-modality apparatus implementing two or more different imaging modalities such as SPECT, PET, CT, or MR. Moreover, in the case of calibration of CBCT data it is contemplated to apply the configuration-specific differential CBCT calibration without also applying the air scan template correction (performed by the sub-module 62). Conversely, it is also contemplated in the case of CBCT data to apply the air scan template correction without also applying the configuration-specific differential CBCT calibration. In the case of a SPECT/CBCT apparatus, it is contemplated to apply configuration-specific differential CBCT calibration and/or air scan template correction without also applying configuration-specific differential SPECT calibration, or vice versa.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A method comprising:
  acquiring cone-beam computed tomography (CBCT) imaging data of a subject using a CBCT radiological imaging apparatus including a CBCT detector array;
  adjusting the air scan template by a constant intensity scale that is constant for all detector pixels of the detector array to generate an up-to-date air scan template;
  calibrating the CBCT imaging data acquired of the imaging subject using the up-to-date air scan template to generate calibrated CBCT imaging data; and
  reconstructing the calibrated CBCT imaging data to generate an image of the imaging subject.

2. The method of claim 1, further comprising:
  determining the constant intensity scale based upon intensity of at least one air pixel measured during the acquiring of the CBCT imaging data of the imaging subject.

3. The method of claim 1, further comprising:
  computing the constant intensity scale based upon at least one ratio between an intensity of an air pixel measured during a frame of the acquiring of the CBCT imaging data of the imaging subject and the corresponding pixel of the corresponding frame of the air scan template.

4. The method of claim 1, further comprising:
  computing the constant intensity scale based upon an exposure history of the CBCT detector array of the CBCT radiological imaging apparatus.

5. The method of claim 1, wherein the calibrating comprises:
  computing line integral values for the CBCT imaging data acquired of the imaging subject using the up-to-date air scan template.

6. A system comprising:
  a cone-beam computed tomography (CBCT) radiological imaging apparatus; and
  a processing device configured to cooperate with the CBCT radiological imaging apparatus to perform a method as set forth in claim 1.

7. A non-transitory storage medium storing instructions executable by a digital processing device to perform a method as set forth in claim 1.

8. A comprising:
acquiring imaging data using an active imaging modality of a tomographic radiological imaging apparatus;
updating a calibration based on current information about the tomographic radiological imaging apparatus to generate an up-to-date calibration, wherein the updating comprises:
selecting a configuration-specific calibration update corresponding to a configuration of an imaging modality the tomographic radiological imaging apparatus that is idle or parked at the time of the acquiring; and
adjusting calibration parameters of the calibration in accordance with the configuration-specific calibration update to generate the up-to-date calibration;
calibrating the imaging data using the up-to-date calibration to generate calibrated imaging data; and
reconstructing the calibrated imaging data to generate an image.

9. The method of claim 2, wherein:
the idle or parked imaging modality includes one or more idle or parked radiation detectors;
the selecting comprises selecting a configuration-specific differential calibration parameter based at least in part on a configuration of the one or more idle or parked radiation detectors at the time of the acquiring; and
the updating comprises adjusting at least one calibration parameter of the calibration based on the selected configuration-specific differential calibration parameter.

10. The method of claim 9, wherein the active modality is one of cone-beam computed tomography (CBCT) and single photon emission computed tomography (SPECT) and the idle or parked modality is the other of CBCT and SPECT.

11. The method of claim 10, wherein the first modality is CBCT, the second modality is SPECT, and the selecting comprises selecting a configuration-specific differential CBCT calibration parameter based at least on an identification of collimator type installed on the one or more SPECT radiation detectors at the time of the acquiring of the CBCT imaging data.

12. The method of claim 8, wherein the selecting comprises selecting a configuration-specific calibration update based at least on an accessory component installed on a radiation detector of the tomographic radiological imaging apparatus.

13. The method of claim 12, wherein the accessory component is selected from a group consisting of a one or more anti-scatter grids, or no anti-scatter grid.

14. A system comprising:
a tomographic radiological imaging apparatus configured to acquire data, the tomographic radiological imaging apparatus being a multi-modality apparatus comprising an active imaging modality that acquires the imaging data and an idle or parked imaging modality that is idle or parked at the time of acquisition of the imaging data; and
a calibration module configured to:
update an active imaging modality calibration based at least in part on a configuration of the idle or parked imaging modality of the tomographic radiological imaging apparatus during the acquisition of the imaging data, and
calibrate the imaging data using the updated active imaging modality calibration to generate calibrated imaging data; and
an image reconstruction module configured to reconstruct the calibrated imaging data to generate an image.

15. The system as set forth in claim 14, wherein the calibration module is configured to update the active imaging modality calibration based at least in part on an accessory component installed on a radiation detector of the idle or parked tomographic radiological imaging modality during the acquisition of the imaging data.

16. A system comprising:
a tomographic radiological imaging apparatus configured to acquire cone beam computed tomography (CBCT) imaging data of an imaging subject;
a calibration module configured to:
compute an intensity scale factor based on an air pixel extracted from a frame of the CBCT imaging data acquired of the imaging subject,
update an air scan template by applying the computed intensity scaling factor to the air scan template to generate an updated air scan template, and
calibrate the CBCT imaging data acquired of the subject using the updated air scan template to generate calibrated imaging data; and
an image reconstruction module configured to reconstruct the calibrated imaging data to generate an image of the imaging subject.

17. A non-transitory storage medium storing instructions executable by a digital processor to perform a method comprising:
causing a tomographic radiological imaging apparatus to acquire imaging data;
updating a calibration acquired with an idle or parked imaging modality of the tomographic radiological imaging apparatus in a first configuration to compensate for acquiring the imaging data with the idle or parked imaging modality in a second configuration different from the first configuration;
applying the updated calibration to the imaging data; and
reconstructing the calibrated imaging data to generate an image.

18. A non-transitory storage medium storing instructions executable by a digital processor to perform a method comprising:
causing a computed tomography (CT) radiological imaging apparatus to acquire CT imaging data of an imaging subject;
identifying one or more air pixels in the CT imaging data acquired of the imaging subject;
calibrating the acquired CT imaging data acquired of the imaging subject to generate calibrated CT imaging data wherein the calibrating includes computing absorption line integrals using $I_o$ values calibrated based on the one or more air pixels identified in the CT imaging data acquired of the imaging subject; and
reconstructing the calibrated CT imaging data to generate an image of the imaging subject.

* * * * *